United States Patent
Fogel

(12)
(10) Patent No.: US 6,689,816 B2
(45) Date of Patent: Feb. 10, 2004

(54) TREATMENT OF POSTTRAUMATIC STRESS DISORDER, OBSESSIVE-COMPULSIVE DISORDER AND RELATED NEUROPSYCHIATRIC DISORDERS

(75) Inventor: Barry S. Fogel, Waban, MA (US)

(73) Assignee: Synchroneuron, Waban, MA (US)

(*) Notice: Subject to any disclaimer, the term of this patent is extended or adjusted under 35 U.S.C. 154(b) by 42 days.

(21) Appl. No.: 10/087,357

(22) Filed: Mar. 1, 2002

(65) Prior Publication Data

US 2002/0119912 A1 Aug. 29, 2002

Related U.S. Application Data

(63) Continuation of application No. 09/273,036, filed on Mar. 19, 1999, now Pat. No. 6,391,922, which is a continuation-in-part of application No. 09/006,641, filed on Jan. 13, 1998, now Pat. No. 5,952,389.

(51) Int. Cl.[7] ............................................. A01K 31/115
(52) U.S. Cl. ........................ 514/702; 514/702; 514/704
(58) Field of Search .................................. 514/702, 704

(56) References Cited

U.S. PATENT DOCUMENTS 6,391,922 B1 * 5/2002 Fogel .......................... 514/702

\* cited by examiner

*Primary Examiner*—Theodore J. Criares
(74) *Attorney, Agent, or Firm*—Choate, Hall & Stewart

(57) ABSTRACT

The present invention describes a novel treatment for neuropsychiatric disorders, including anxiety disorders, mood disorders, psychotic disorders, somatoform disorders, and neuropsychiatric symptoms resulting from movement disorders. The treatment of the present invention utilizes any agent that simultaneously act as NMDA-type glutamate receptor antagonists and GABA-A receptor agonists. Preferably these two activities are characteristic of a single agent, for example acamprosate (calcium N-acetylhomotaurinate). Alternatively, separate agents having these activities can be combined as a compound or mixture and thereby administered together. The invention also provides for a third agent that acts as a non-competitive NMDA-receptor blocking agent or ion channel blocker, that augments the effect of the primary treatment. A particularly preferred ion channel blocking agent is magnesium.

8 Claims, No Drawings

TREATMENT OF POSTTRAUMATIC STRESS DISORDER, OBSESSIVE-COMPULSIVE DISORDER AND RELATED NEUROPSYCHIATRIC DISORDERS

PRIORITY INFORMATION

The present application is a Continuation application of U.S. patent application Ser. No. 09/273,036 filed Mar. 19, 1999, now U.S. Pat. No. 6,391,922, which is a Continuation-in-part application of U.S. patent application Ser. No. 09/006,641 now U.S. Pat. No. 5,952,389, filed Jan. 13, 1998, the entire contents of which are incorporated herein by reference.

BACKGROUND OF THE INVENTION

The present invention relates to novel drug treatments for neuropsychiatric disorders, for example anxiety disorders, psychotic disorders, mood disorders and somatoform disorders. These treatments relieve symptoms of disorders characterized by repetitive, stereotyped, an unwanted, intrusive, or involuntary thoughts, perceptions, or behaviors. These include posttraumatic stress disorder, obsessive-compulsive disorder, somatization disorder, hypochondriasis, and body dysmorphic disorder. Contemporary drug therapy for these conditions is limited in efficacy, with many patients continuing to have symptoms despite treatment. Antidepressants, mood stabilizers, anti-anxiety drugs, and antipsychotic drugs all have been used to treat them. Even when they provide some relief, persistent intrusive, repetitive mental phenomena may remain as a distressing symptom. Thus, when a person with posttraumatic stress disorder is treated with an antidepressant, mood may improve while "flashbacks" of the traumatic event continue.

Clearly, there is a need for additional medications efficacious for the treatment of these disorders, and especially for medications that suppress or eliminate the recurrent unwanted, intrusive, or involuntary thoughts, perceptions and behaviors characteristic of those disorders. Such medications might also be used to reduce such symptoms when they occur as part of another psychiatric syndrome, such as depression or schizophrenia, or when they are incidental to a neurological disorder such as Tourette's syndrome or Huntington's disease.

I begin by reviewing the prototypical conditions for which the novel treatment is useful:

Posttraumatic Stress Disorder (PTSD)

Description of PTSD

Posttraumatic stress disorder is an immediate or delayed response to a catastrophic event, characterized by the following features:

"re-experiencing the trauma, psychic numbing or avoidance of stimuli associated with the trauma, and increased arousal. Re-experiencing phenomena include intrusive memories, flashbacks, nightmares, and psychological or physiological distress in response to trauma reminders. Intrusive memories are spontaneous, unwanted, distressing recollections of the traumatic event. Repeated nightmares contain themes of the trauma or a highly accurate and detailed re-creation of the actual event(s). Flashbacks are dissociative states in which components of the event are relived, and the person feels as if he or she is experiencing the event for a few seconds for as long as days. Reactivity to trauma-related stimuli can involve intense emotional distress or physical symptoms similar to those of a panic attack, when the patient is exposed to sights, sounds, smells or events that were present during the traumatic event. Avoidance may include thoughts, feelings, situations or activities that are reminders of the trauma. Numbing may occur through amnesia, emotional detachment, restricted affect, or loss of interest in activities. Increased arousal may include insomnia, irritability, hypervigilance, increased startle response, or impaired concentration. This disorder can have pervasive effects on an individual's interpersonal behavior and all spheres of his or her life." (Charney D S et al.: Neurobiological mechanisms of human anxiety. In Fogel B S, Schiffer R B, Rao S M: Neuropsychiatry. Baltimore: Williams & Wilkins, 1996, pp. 257–286).

Epidemiology of PTSD

Among American veterans of the Vietnam War, the lifetime prevalence rate of PTSD was estimated as 31% in men and 27% in women; current prevalence estimates were 15% and 8.5%, respectively. In a survey of female victims of crime, the lifetime prevalence of PTSD was 13% and the current prevalence 3%. Overall, PTSD affects 2% or more of the US population (Charney et al., supra). Among people with work-related injuries, the rate of PTSD may exceed one-third, or even one-half, if people with partial PTSD syndromes are included (Asmundson G J, et al.: Posttraumatic stress disorder and work-related injury. J Anxiety Disord, 12:57–69, January–February 1998). Manifestly, PTSD is a significant public health problem.

Complications and Comorbidity

There is a strong association between PTSD and substance abuse, especially alcoholism. (Coffey S F, et al.: Screening for PTSD in a substance abuse sample: psychometric properties of a modified version of the PTSD Symptom Scale Self-Report. J Trauma Stress, 11:393–9, April 1998). In addition, chronic PTSD can increase a person's long-term risk of a broad range of chronic diseases. Long-term follow up of men exposed to severe combat-related stress showed that PTSD significantly increased the risk of developing disorders of the circulatory, digestive, and respiratory systems as well as, infectious diseases, and neurological and psychiatric disorders other than PTSD (Boscarino J A: Diseases among men 20 years after exposure to severe stress: implications for clinical research and medical care. Psychosom. Med., 59:605–14, November–December 1997).

Various studies over the past decade have identified risk factors for the development of PTSD following an acute traumatic event. These include lower intelligence, a less developed narrative of the traumatic event, a history of prior trauma, and a rapid heart rate at the time of post-trauma medical examination. If a person develops an acute stress disorder after a major traumatic event (i.e., immediately displays symptoms resembling those of PTSD), that individual is likely to continue having symptoms, and eventually warrant, a diagnosis of PTSD. These considerations imply that a population at high risk for PTSD can be identified. If there were a non-toxic drug that significantly and specifically reduced the symptoms of PTSD, it could be used in this high-risk population to prevent the development of PTSD.

Pathophysiology of PTSD

The pathophysiology of PTSD involves disturbances in brain systems involved with reaction to stress, including the hypothalamic-pituitary-adrenal axis, and systems involving norepinephrine, serotonin, endogenous opiates, and endogenous ligands for benzodiazepine receptors. PTSD involves overactivity of the noradrenergic arousal systems, with relative underactivity of the hypothalamic-pituitary-adrenal axis (Henry JP: Psychological and physiological responses to stress: the right hemisphere and the hypothalamo-pituitary-adrenal axis, an inquiry into problems of human bonding. Acta Physiol Scand Suppl, 640:10–25, 1997). On the other hand, underactivity of endogenous opiate mechanisms may contribute to the symptoms of PTSD. (Baker D G, et al.: Cerebrospinal fluid and plasma beta-endorphin in combat veterans with post-traumatic stress disorder. Psychoneuroendocrinology, 22:517–29, October 1997)

Animal experiments suggest NMDA receptor-mediated processes are likely to be involved in the establishment of anxiety-like behavior following stressful events. The latter induce long-term potentiation (LTP) affecting connections within the amygdala, and between the amygdala and its efferents. A natural inference is that NMDA-receptor mediated processes are involved in the development of PTSD in humans (Adamec R: Transmitter systems involved in neural plasticity underlying increased anxiety and defense: implications for understanding anxiety following traumatic stress. Neuroscience and biobehavioral reviews 21(6):755–65, 1997). In a recent review, two Israeli investigators described a central role of NMDA receptors in posttraumatic stress disorder, as well as schizophrenia, alcoholism and major depression. They proposed that agents that modulate NMDA receptor function would be useful in treating all of these disorders (Heresco-Levy U, Javitt D C: The role of N-methyl-D-aspartate (NMDA) receptor-mediated neurotransmission in the pathophysiology and therapeutics of psychiatric syndromes. Eur Neuropsychopharmacol May 1998;8(2):141–52). They did not, however, propose acamprosate in the treatment of PTSD, nor the combination of NMDA receptor and GABA-A receptor actions in the treatment of these disorders.

In addition to the amygdala and its connections, PTSD involves dysfunction of the caudate nuclei. Lucey et al. (1997) in a SPECT study, showed that PTSD symptoms were negatively correlated with caudate blood flow, with the correlation stronger on the right side. (Lucey J V, et al.: Brain blood flow in anxiety disorders. OCD, panic disorder with agoraphobia, and post-traumatic stress disorder on 99mTcHMPAO single photon emission tomography (SPET). Br J Psychiatry, 171:346–50, October 1997).

The role of GABA in the pathophysiology of PTSD has not been settled. Benzodiazepines may relieve anxiety associated with PTSD. However, they usually do not do much for the specific symptoms of the disorder. In a study of trauma survivors, early administration of high-potency benzodiazepines following the trauma did not prevent the development of PTSD, even though it did reduce physiological arousal, e.g. resting heart rate (Gelpin E, et al.: Treatment of recent trauma survivors with benzodiazepines: a prospective study. J Clin Psychiatry, 57:390–4, September 1996). Moreover, the benzodiazepine antagonist flumazenil did not produce an increase in anxiety of PTSD symptoms in patients with PTSD (Randall P K, et al.: Effects of the benzodiazepine antagonist flumazenil in PTSD. Biol Psych 38(5):319–24, 1995).

Drug treatment of PTSD

Drug treatment of PTSD has had limited success. Not surprisingly in view of this, a wide range of medications have been tried. Individual patients have benefited from various drugs, but none have emerged as a standard treatment. Perhaps the most predictable benefits come from treating manifest anxiety and depression with anti-anxiety and antidepressant drugs, and from treating psychotic symptoms with antipsychotic drugs. These treatments relieve suffering and can improve function, but do not in general alter the core symptoms of intrusive thoughts and images, hyperarousal, and emotional numbing.

Classes of medications that have helped individual patients with PTSD include benzodiazepines, dopamine antagonists (neuroleptics), specific serotonin reuptake inhibitors (SSRIs), tricyclic antidepressants, antiepileptic drugs (AEDs), lithium, beta-adrenergic blockers, and clonidine (an alpha 2-adrenergic agonist), to name a few. Cyproheptadine, a serotonin receptor blocker, has shown efficacy for suppression of nightmares in patients with PTSD (Gupta S, et al.: Efficacy of cyproheptadine for nightmares associated with posttraumatic stress disorder. Compr Psychiatry, 39:160–4, May–June 1998). Recently, risperidone, an atypical neuroleptic, was shown to suppress intrusive mental phenomena in children and adolescents with PTSD—though it did not do so completely (Horrigan J, presentation at the American Academy of Child and Adolescent Psychiatry annual meeting, October 1998; reported in Psychiatric News, Dec. 18, 1998.)

A full-text patent search on "treatment" and "posttraumatic stress disorder" yielded 13 relevant patents (U.S. Pat. Nos. 5,028,612; 4,962,128; 5,484,794; 5,488,056; 5,574,028; 5,574,029; 5,574,053; 5,708,014; 5,726,193; 5,763,457; 5,776,969; 5,852,036; 5,852,037), none of which dealt with glutamate or GABA-related mechanisms. Several patents on chemicals affecting NMDA-glutamate neurotransmission include PTSD in a long list of psychiatric disorders potentially treatable with those chemicals. To date, however, no specific glutamate antagonist has been tested as a treatment for PTSD in humans. In particular, there is no literature suggesting or reporting the combination of NMDA receptor antagonists and GABA-A agonists, or the use of a drug with combined NMDA antagonist-GABA-A agonist actions, in the treatment of PTSD.

One recent publication reviews "The role of NMDA receptor-mediated neurotransmission in the pathophysiology and therapeutics of psychiatric syndromes" (Heresco-Levy U, Javitt, D C, European Neuropsychopharmacology 8(1998):L 141–152). The authors note that NMDA antagonists infused into the amygdala can block the acquisition of an enhanced startle response, and infer that glutamate-dependent long-term potentiation may be critical for the development of conditioned fear and encoding of traumatic memories. However, they suggest that enhancers of NMDA receptor-mediated neurotransmission might have therapeutic effects in PTSD. They go on to state that up-regulators of NMDA neurotransmission might also reverse or prevent the cognitive deficits associated with PTSD.

Heresco-Levy and Javitt also describe the hypothesis that schizophrenia is a hypoglutamatergic state, while proposing that excessive NMDA-glutamate neurotransmission may underlie certain cases of major depression. D-cycloserine, a mixed agonist-antagonist binding to the glycine site on the NMDA receptor, is advanced as a treatment for both conditions. It is evident from this and other reviews (not enumerated here) that abnormalities of NMDA-glutamate neurotransmission are associated with psychiatric symptoms and syndromes and the various modulators of NMDA-glutamate neurotransmission are candidates for therapeutic use in mental disorders. However, available literature does not propose that NMDA antagonists would be therapeutic for PTSD, OCD, or the repetitive thoughts, perceptions, and actions that may occur as part of other neuropsychiatric disorders. The literature is totally silent on treatment with agents that combine NMDA antagonism with GABA-A agonism.

In summary, PTSD is a common disorder with significant morbidity and frequent complications, which include physical illness and substance abuse. Available drug treatment is limited in efficacy. Although a role of glutamate and NMDA receptors in the establishment of PTSD is suggested by animal models, specific NMDA receptor antagonists have not been reported as a treatment for PTSD in human patients. There exists the need for additional drugs to treat PTSD, that can provide relief of specific symptoms of the disorder, without unacceptable toxicity. An efficacious drug treatment might not only treat PTSD, but might prevent it if given soon after stress.

Obsessive-Compulsive Disorder

Description of OCD

Obsessive-compulsive disorder (OCD) is an anxiety disorder characterized by recurrent obsessions or compulsions sufficient to cause marked distress. These behaviors are time-consuming, or significantly interfere with the person's normal functioning, social activities, or relationships. Obsessions are recurrent ideas, thoughts, images, or impulses that enter the mind and are persistent, intrusive, and unwelcome. Attempts are made to ignore or suppress the thoughts, or to neutralize them with some other thought or action. The individual recognizes them as a product of his or her own mind. Compulsions are repetitive, purposeful behaviors performed in response to an obsession, and are designed to neutralize or prevent discomfort or some dreaded event or situation. However, the activity is excessive, or not connected realistically with that which it is designed to prevent. The affected person recognizes that his or her behavior is unreasonable. (Robertson M M, Yakely J: Gilles de la Tourette syndrome and obsessive-compulsive disorder. In: Fogel B S, Schiffer R B, Rao S M: Neuropsychiatry. Baltimore: Williams & Wilkins, 1996, pp.827–870).

Epidemiology of OCD

Estimates of the lifetime prevalence of OCD in the US have ranged from 1.9% to 3.2%. Milder forms of obsessive-compulsive behavior are even more common. The lifetime risk of developing OCD within a normal life span has been estimated at 5.4% (Bland R C, Newman S C, Om H: Epidemiology of psychiatric disorders in Edmonton. Acta Psychiatr Scand 77 (Suppl): 338, 1988). The disorder usually is chronic, with only about 1/3 of patients having spontaneous remissions (Robertson and Yakely, supra).

Pathophysiology of OCD

OCD is currently thought to be due to excessive activity in neural circuits involving the orbital frontal cortex, the anterior cingulate region, the caudate nucleus and the thalamus. Recurrent activity in these circuits produces the characteristic recurrent, stereotypic obsessions and compulsions. This localization of OCD has been supported by a number of brain imaging studies with differing methodologies and overlapping results (Saxena et al.: Neuroimaging and frontal-subcortical circuitry in obsessive-compulsive disorder. Br J Psychiatry Suppl 1998;(35):26–37). Saxena and colleagues hypothesize hyperactivity of an orbital frontal-subcortical circuit, due to an imbalance of tone in direct versus indirect striato-pallidal pathways. Neuropsychological testing also suggests dysfunction of orbital frontal structures and their subcortical connections (Schmidtke K, et al.: Cognitive frontal lobe dysfunction in obsessive-compulsive disorder. Biol Psychiatry, 43:666–73, May 1, 1998; Purcell R, et al.: Cognitive deficits in obsessive-compulsive disorder on tests of frontal-striatal function. Biol Psychiatry, 43:348–57, Mar 1, 1998).

From the standpoint of neurotransmitter function, the broadest scientific consensus supports a role for serotonergic system dysfunction in OCD. (Robertson and Yakely, supra) Of greatest importance is the observation that serotonin reuptake inhibitors (SRIs) are the most consistently effective drug treatments of the disorder. In addition, studies have shown differences in serotonergic transmission between OCD patients and controls. As one example of many, patients with OCD have a lesser increase in prolactin after d-fenfluramine challenge than do normal controls. (D-fenfluramine is a SRI). Furthermore, patients with more blunting of the prolactin response tend to have worse symptoms of OCD (Monteleone, et al.: Prolactin response to d-fenfluramine in obsessive-compulsive patients, and outcome of fluvoxamine treatment. Br J Psychiatry 170:554–7, June 1997).

Dopamine may also have a role in producing the symptoms of OCD. Direct and indirect dopamine agonists, including levodopa and amphetamine, can produce stereotypical 'ritual-like' behavior in animals, and the use of stimulants in humans has been documented to produce repetitive actions resembling the compulsive behaviors of OCD (Robertson and Yakely, supra). The ability of dopamine antagonists to augment the therapeutic effects of SRIs is compatible with a hypothesis of dopaminergic hyperactivity at synapses involved in symptom production.

More recent research has suggested a role for glutamate in the production of OCD symptoms, and perhaps an ancillary role for a deficiency of GABA. Moore et al. (J. Am Acad. Child Adolesc. Psychiatry, June, 1998 37 (6):663–667) report a case of a 9-year old boy with OCD studied by PET scanning before and after successful treatment with paroxetine, a specific serotonin reuptake inhibitor (SSRI). They found major changes in glutamate resonance in the caudate region. They inferred that serotonin-glutamate interaction was involved in the pathophysiology of OCD. In a study of benzodiazepine receptors in lymphocyte membranes of patients with anxiety disorders, including OCD, patients with OCD had 25% fewer benzodiazepine binding sites than normal controls (Rocca P et al.: Peripheral-type benzodiazepine receptors in anxiety disorders. Acta Psychiatrica Scandinavica 84:6: 537–544, December 1991). This finding suggests that GABA-linked inhibition may be lacking in patients with OCD, as well as in other anxiety disorders.

Drug Treatment of OCD

SRIs (i.e., SSRIs plus clomipramine, a tricyclic antidepressant with predominant serotonin reuptake inhibition) are the mainstay of drug treatment for OCD. However, not all patients with OCD respond to SRIS, some do not tolerate them, and many have only a partial response. (Rasmussen S A, Eisen J L: Treatment strategies for chronic and refractory obsessive-compulsive disorder. J Clin Psychiatry, 58 Suppl 13:9–13, 1997). In a 1997 review, Henrietta Leonard notes that "The only agents that have shown significant improvement as augmenting agents to an SRI/SSRI in systematic trials have been clonazepam and haloperidol." (Leonard H: New developments in the treatment of obsessive-compulsive disorder. J Clin Psychiatry, 58 Suppl 14:39–45; discussion 46–7, 1997). Clonazepam is a GABA-A agonist with effects on serotonergic transmission; haloperidol a dopamine receptor blocker. Other second-line or augmenting agents, for which there is less supporting evidence, include other dopamine antagonists, lithium, clonidine (an alpha 2-adrenergic agonist), monoamine oxidase inhibitors (MAOIs), buspirone (a serotonin 1A agonist), and various other drugs that affect serotonergic transmission. Dopamine antagonists may be more useful in augmenting the response of OCD to SSRIs in patients with a personal or family history of tics (McDougle C J: Update on pharmacologic management of OCD: agents and augmentation. J Clin Psychiatry, 58 Suppl 12:11–7, 1997).

Somatoform Disorders: Somatization Disorder, Conversion Disorder, Hypochondriasis, and Body Dysmorphic Disorder Description of Somatoform Disorders Somatoform disorders are conditions characterized by physical symptoms without a known physiological explanation, and presumed to be caused by psychological processes. "The common feature of the Somatoform Disorders is the presence of physical symptoms that suggest a general medical condition (hence the term somatoform) and are not fully explained by a general medical condition, by the direct effects of a substance, or by another mental disorder (e.g., Panic Disorder)." (American Psychiatric Association: Diagnostic and Statistical Manual of Mental Disorders, Fourth Edition. Washington, D.C., American Psychiatric Association, 1994). Somatoform disorders are divided into a number of syndromes; complete, formal diagnostic criteria for them can be found in the Diagnostic and Statistical Manual of Mental Disorders (American Psychiatric Association, supra). Of relevance to this application are three disorders in which repetitive, unwanted stereotyped thoughts, (in this case thoughts about somatic symptoms), are prominent:

1) Somatization Disorder is a chronic condition with onset before age 30 and duration greater than 6 months, characterized by numerous somatic complaints without demonstrable general medical causes, involving several different organ systems, and including four pain symptoms, two gastrointestinal symptoms, one sexual symptom, and one neurological symptom.
2) Conversion Disorder: unexplained sensory or motor complaints without a demonstrable general medical or neurological cause. Complaints are assessed by the clinician as being related to psychological factors.
3) Hypochondriasis is a morbid preoccupation with the fears of having, or the belief that one already has, a serious disease. These are accompanied by misinterpretation of bodily symptoms and evidence from physical examination and laboratory tests that exclude the disease with which the individual is preoccupied. The fears or beliefs cause distress and/or functional impairment, last 6 months or more, and are not relieved by medical evaluation and reassurance.
4) Body Dysmorphic Disorder: is a morbid preoccupation with an imagined defect in appearance, or grossly disproportionate concern about an actual minor physical anomaly. It is often associated with compulsive behaviors such as picking at the skin, reassurance seeking, and mirror checking (Phillips K A: Body dysmorphic disorder: diagnosis and treatment of imagined ugliness. J Clin Psychiatry, 57 Suppl 8( ):61–4).

Epidemiology of Somatoform Disorders

Estimates of prevalence vary, depending on the population studied. Obviously, the disorders are much more common in clinical samples than in the general population. However, even in the general population, the prevalence is substantial. A few recent studies illustrate this point.

1) In a community study carried out by general practitioners in two neighborhoods in Florence, Italy, the authors reported the following 1-year prevalence figures: 0.7% for somatization disorder, 0.3% for conversion disorder, 4.5% for hypochondriasis, and 0.7% for body dysmorphic disorder. (Faravelli C, et al.: Epidemiology of somatoform disorders: a community survey in Florence. Soc Psychiatry Psychiatr Epidemiol, 32(1):24–9 January 1997).
2) The prevalence of somatoform disorders in two rural primary care practices was 11.1% (Philbrick J T, et al.: The prevalence of mental disorders in rural office practice. J Gen Intern Med, 11(1):9–15 January 1996).
3) A community survey of Chinese-Americans living in Los Angeles showed a 3.6% prevalence of "neurasthenia", a somatoform disorder not specified in the Diagnostic and Statistical Manual of Mental Disorders, but recognized widely as a discrete syndrome. Neurasthenia has features in common with hypchondriasis and somatization disorder. Of note, these individuals were screened to exclude anxiety disorders or depression as the cause of their somatic symptoms.

Relationship of PTSD to Somatization

Somatoform disorders, like PTSD, involve repetitive unwanted, intrusive or involuntary stereotyped thoughts, perceptions, and behaviors. In addition to this similarity, PTSD, somatization, and dissociation frequently occur together in the same patients. In a study of over 500 individuals who had been exposed to traumatic experiences, PTSD, dissociation, somatization, and affect dysregulation were highly interrelated. (van der Kolk B A, et al.: Dissociation, somatization, and affect dysregulation: the complexity of adaptation of trauma. Am J Psychiatry, 153(7 Suppl):83–93 July 1996). The authors concluded that "PTSD, dissociation, somatization, and affect dysregulation represent a spectrum of adaptations to trauma. They often occur together, but traumatized individuals may suffer from various combinations of symptoms over time." Victims of torture, a most extreme stress, frequently develop a combination of somatization and PTSD (Priebe S; Esmaili S: Long-term mental sequelae of torture in Iran—who seeks treatment? J Nerv Ment Dis, 185(2):74–7 February 1997).

Pathophysiology of Somatoform Disorders

There has been surprisingly little research on the regional brain function in the somatoform disorders in general. However, there has been much work on regional brain function in clinical and experimental pain, using such techniques as PET scanning and functional MRI (fMRI). Similarly, much more is known about the neurochemistry of pain than about the neurochemistry of somatoform disorders. The study of pain is a valuable source of ideas related to the treatment of somatoform disorders, though obviously analgesics are not ipso facto treatments for somatoform disorders, nor would treatments for somatoform disorders necessarily be analgesics. The important link is that emotional distress related to a somatic perception is a common feature of pain and the somatoform disorders mentioned here. The physiological mechanism underlying emotional distress in the somatization disorders is likely to involve limbic system nuclei and pathways related to the emotional (as opposed to the purely sensory) aspects of pain perception. The following section summarizes some facts about pain transmission relevant to the present invention.

GABA, Glutamate, and Pain

Patients with some types of somatoform disorders experience pain. Pain transmission and modulation in the spinal cord are strongly affected by GABA and glutamate. NMDA-receptor mediated processes are involved in the development of states of hypersensitivity to pain. "Information concerning amplification systems in the spinal cord, such as the NMDA receptor, is a step toward understanding why and how a painful response is not always matched to the stimulus. Such events have parallels with other plastic events such as long-term potentiation (LTP) in the hippocampus" (Dickenson A H, et al.: The pharmacology of excitatory and inhibitory amino acid-mediated events in the transmission and modulation of pain in the spinal cord. Gen Pharmacol, 28(5):633–8 May 1997). Ultimately, the balance of NMDA-mediated amplification and GABA-mediated attenuation determines the intensity of the pain signal transmitted from the spinal cord to the brain. Dickenson et al. (supra) observe that in inflammatory conditions, increased GABA activity offsets increased glutamate activity, while in neuropathic pain, it does not. This corresponds to the clinical observation that neuropathic pain may be more excruciating than pain due to tissue damage and inflammation.

Spinal cord stimulation is used clinically to alleviate intractable pain, e.g., from cancer. In animal models, the effect of spinal cord stimulation is to decrease the release of glutamate and aspartate at the dorsal horns, and to increase the release of GABA (Cui J G, et al.: Spinal cord stimulation attenuates augmented dorsal horn release of excitatory amino acids in mononeuropathy via a GABAergic mechanism. Pain, 73(1):87–95 October 1997). This supports the idea that more GABA and less glutamate (in the vicinity of NMDA receptors) is associated with analgesia. The spontaneous activity of dorsal horn neurons is suppressed by GABA and increased by glutamate, via an NMDA-receptor dependent mechanism. Augmented release of GABA partially explains the analgesic benefits of transcutaneous electrical nerve stimulation (TENS). In a cat model, the analgesic effects of electrical stimulation of peripheral nerves were partially blocked by picrotoxin, a GABA-A antagonist—suggesting a GABA-A mediated component (Jeong Y, et al.: Effects of iontophoretically applied naloxone, picrotoxin and strychnine on dorsal horn neuron activities treated with high frequency conditioning stimulation in cats. Yonsei Med J, 36(4):336–47 September 1995).

Based on similar studies involving the brain as well as the spinal cord, central pain, due to damage to the brain or spinal cord, has been attributed to a combination of glutamatergic and GABAergic mechanisms.

"Recent evidence suggests that central pain, i.e., pain due to central nervous system damage, may be due to a deranged neurotransmission between the sensory thalamus and sensory cortical areas. Central pain can be controlled either by opposing glutamate neurotransmission or potentiating GABAergic transmission. It is speculated that a relative hypofunction of the GABAergic inhibition both at thalamic and cortical levels leads to a sectorial excitatory hypertonus in those same areas, A blend of the two should mark each patient. A pharmacological dissection approach is provided that should optimize the treatment, up to now globally poor, of central pain." (Canavero S; Bonicalzi V: The neurochemistry of central pain: evidence from clinical studies, hypothesis and therapeutic implications. Pain, 74(2–3):109–14 February 1998).

Drug Treatment of Somatoform Disorders

Among the somatoform disorders, Body Dysmorphic Disorder has the best established drug treatment, SRIs. (Phillips, supra; Phillips K A, et al.: Efficacy and safety of fluvoxamine in body dysmorphic disorder. J Clin Psychiatry, 59(4):165–71 April 1998; Perugi G, et al.: Fluvoxamine in the treatment of body dysmorphic disorder (dysmorphophobia) Int Clin Psychopharmacol, 11 (4):247–54 December 1996). This is perhaps not surprising, in view of its similarity to OCD, which also responds to SRIs in many cases. Phillips points out that augmentation with buspirone or neuroleptics may be helpful in Body Dysmorphic Disorder just as it is in OCD. However, the investigators cited above note that only about ⅔ of the patients they treated improved with SRIS.

For the other somatoform disorders, antidepressants of various kinds are most often used. They often are warranted because the patient has concurrent major depression or dysthymia, but they clearly can work in cases where the somatic symptoms are not accompanied by obvious depression. The concept of "masked depression" or "depressive equivalent" has been used for decades to explain these responses (Downes-Grainger E, et al.: Clinical factors associated with short-term changes in outcome of patients with somatized mental disorder in primary care. Psychol Med, 28(3):703–11 May 1998)

When patients' somatic complaints and concerns reach delusional proportions, they may get relief from neuroleptic drugs. These, of course, have problematic long-term side effects such as tardive dyskinesia.

Some patients may get transient relief of somatic symptoms and concerns from opiates or benzodiazepines. Unfortunately, tolerance develops. Prescription drug dependence or abuse can result.

The use of SRIs for Body Dysmorphic Disorder represents significant progress; so does the awareness that many patients who amplify symptoms will benefit from antidepressant drugs, even if they do not show manifest depression. Nonetheless, not all patients will respond to these treatments. For Somatization Disorder, Conversion Disorder, and Hypochrondriasis, drug treatment to date has been less satisfactory.

The Context of the Invention

In summary, PTSD, OCD and four somatoform disorders—Somatization Disorder, Conversion Disorder, Hypochondriasis, and Body Dysmorphic Disorder, are neuropsychiatric disorders characterized by intrusive, repetitive stereotyped thoughts, perceptions and behaviors that cause significant distress and disability for a substantial portion of the general population. A widely effective and tolerable drug treatment would significantly improve the treatment prospects for patients suffering from these neuropsychiatric disorders. In addition, it would offer a meaningful new treatment option in psychopharmacology—distinct from antidepressants, anti-anxiety drugs, mood stabilizers (e.g., lithium, valproate), and neuroleptics. Thus, it would offer a new method of treating residual symptoms of patients partially responsive to treatment with any of these established classes of psychotropic agents.

SUMMARY OF THE INVENTION

The present invention provides a method for treating: (1) neuropsychiatric disorders such as posttraumatic stress disorder (PTSD), obsessive-compulsive disorder (OCD) and somatoform disorders, for which it alleviates characteristic symptoms; and (2) symptoms of other neuropsychiatric disorders such as Schizophrenia, Major Depression and Bipolar Disorder, whenever their symptoms include recurrent unwanted, intrusive or involuntary stereotyped, thoughts, perceptions, or behaviors. More generally, the present invention provides a method for treating any neuropsychiatric disorder, including any anxiety disorder, psychotic disorder, mood disorder or somatoform disorder.

In one aspect, the invention provides a method for treating neuropsychiatric disorders by administering a pharmacological agent, that both (i) acts directly or indirectly as an agonist at GABA-A receptors and (ii) decreases NMDA-type glutamate neurotransmission by a direct, indirect or modulatory mechanism. Specific instances include calcium N-acetylhomotaurinate (acamprosate), magnesium N-acetylhomotaurinate, other salts of N-acetylhomotaurinate, derivatives of N-acetylhomotaurinate with similar pharmacodynamic effects on GABA and NMDA-type glutamate neurotransmission, and pro-drugs that are metabolized in the liver, blood, or brain to yield N-acetylhomotaurinate or a derivative with similar pharmacodynamic effects. In another aspect, the present invention provides methods for treating neuropsychiatric disorders by administering more than one pharmacological agent that, in combination, act to increase GABA-A neurotransmission and decrease NMDA-type glutamate neurotransmission.

The present invention also provides a method for treating neuropsychiatric disorders by combining memantine, magnesium, or a non-competitive NMDA receptor antagonist with acamprosate, or another compound or mixture thereof (specifically including those enumerated in the previous paragraph) that simultaneously decreases the postsynaptic response to glutamate at NMDA-type receptors and also directly or indirectly increases GABA-A transmission. In preferred embodiments, magnesium is used as a non-competitive NMDA receptor antagonist. Alternatively, a GABA-A agonist can be combined with a compound that has both NMDA antagonist activity and GABA-A agonist activity.

In other preferred embodiments, the present invention sets forth that magnesium can augment the effect of pharmacological agents used to treat neuropsychiatric disorders including anxiety disorders such as posttraumatic stress disorder and obsessive-compulsive disorder, somatoform disorders, mood disorders, psychotic disorders and other disorders with recurrent stereotyped, thoughts, perceptions, or behaviors that are unwanted, intrusive, or involuntary. Synergistic activity of magnesium and pharmacological agents that act to simultaneously decrease NMDA-glutamate neurotransmission and augment GABA-A neurotransmission has been demonstrated previously in treatment of movement disorders. (This is detailed in co-pending application Ser. No. 09/193,892, which is incorporated herein by reference.) Thus, in the present invention, magnesium is combined with pharmacological agents that act to simultaneously decrease NMDA-glutamate neurotransmission and augment GABA-A neurotransmission to treat neuropsychiatric disorders.

In other embodiments, any combination of agents that act as NMDA receptor antagonists together with one or more agents that facilitate GABA-A neurotransmission (by acting as GABA-A receptor agonists, by increasing GABA-A release, by inhibiting the re-uptake of GABA from the synapse, or by increasing the post-synaptic response to GABA-A receptor stimulation), with or without magnesium, are used for treatment of neuropsychiatric disorders.

A pill combining agents that act as NMDA-type glutamate receptor antagonists, GABA agonists and magnesium is proposed as a specific vehicle for the delivery of this combined therapy. In addition, other oral preparations are suggested; the mixture can be delivered in a syrup, elixir, or time-release capsule. The latter is suggested as one method for prolonging the duration of action of a dose of the mixture.

In a final embodiment, agents or combinations of agents having both the activity of NMDA antagonism and GABA-A agonism are used to prevent development of PTSD in individuals exposed to extreme stress. Alternatively compositions with combined NMDA antagonism and GABA-A agonism are used to prevent symptoms of an acute stress reaction from continuing or evolving into PTSD. It is particularly preferred that these agents are used to prevent the development of substance abuse, for example alcoholism, subsequent to extreme stress or as a complication of posttraumatic stress disorder.

Definitions

"Effective": "Effective" as used herein in reference to dose refers to the administration of a specific amount of a pharmacologically active agent tailored to each individual patient manifesting symptoms of neuropsychiatric disorder, sufficient to cause a reduction or improvement in any of the associated symptoms, with tolerable adverse effects. Experimentally, doses of acamprosate ranging from 333 mg to 666 mg administered three to four times daily are effective. A person skilled in the art will recognize that the optimal dose of a pharmaceutical agent administered will vary from one individual to another. Dosage in individual patients should take into account the patient's height, weight, rate of absorption and metabolism of the medication in question, and the stage of the disorder to be treated, as well as what other pharmacological agents are administered concurrently.

"Non-toxic": As used herein, "non-toxic" refers to the administration of a dose of a medication in question, wherein the active components in the composition cause no adverse effects intolerable to the patient to whom it is administered, or judged by the physician to be a contraindication to continuing the medication.

"Acamprosate": As used herein, "acamprosate" refers to calcium N-acetylhomotaurinate. These two terms may be used interchangeably. "N-acetylhomotaurinate" and "acetylhomotaurinate" are used interchangeably.

"Acamprosate and related compounds": "Acamprosate and related compounds" refers to calcium acetylhomotaurinate, magnesium acetyllhomotaurinate, other salts of N-acetylhomotaurinate, and acetylhomotaurine base, and those derivatives of homotaurine or acetylhomotaurine that have similar pharmacodynamic activity with respect to GABA-A and NMDA-type glutamate neurotransmission, and pro-drugs that are metabolized in the blood, liver, or brain to yield acetylhomotaurinate or derivatives with similar pharmacodynamic activity with respect to GABA-A and NMDA-type glutamate transmission. Acamprosate decreases the intracellular response of neurons stimulated by glutamate at the NMDA receptor, and enhances GABA-A transmission, at least in part by an antagonist effect on pre-synaptic GABA-B inhibitory autoreceptors. For ease of expression, I refer to acamprosate and similar compounds with similar CNS pharmacodynamics by various terms which as used herein should be regarded as synonymous: "GABA agonists and NMDA antagonists", "GABA-A agonists and NMDA-antagonists", "agents that increase GABA transmission and decrease NMDA-type glutamate transmission", "GABA agonists and glutamate antagonists", and "up regulators of GABA transmission and down-regulators of NMDA-type glutamate transmission".

"GABA-A transmission": "GABA-A transmission refers to the pharmacodynamic phenomena associated with the activation of GABA-A receptors by GABA. Enhancement of GABA-A transmission may involve increasing the release of GABA, decreasing its metabolism, decreasing the re-uptake of GABA from the synapse, increasing receptor binding, or increasing the cellular effects of receptor binding.

"GABA-A receptor agonist": "GABA-A receptor agonist", as used herein refers to molecules that are capable of enhancing GABA-A transmission (as defined above).

"NMDA receptor antagonist": As used herein, "NMDA receptor antagonist" is any molecule that inhibits or diminishes the postsynaptic response of NMDA-type glutamate receptors to glutamate.

"NMDA-type glutamate neurotransmission": "NMDA-type glutamate Neurotransmission" is used herein to broadly refer to anything that would decrease NMDA-glutamate transmission, whether it acts before the synapse, at the receptor binding site, within the ion channel, within the cell membrane, or inside the neuron. This includes anything that reduces release of glutamate at synapses with NMDA receptors, alters the binding of glutamate to NMDA receptors or alters the number of NMDA receptors.

"Neuropsychiatric disorder": As used herein, "neuropsychiatric disorder" is used synonymously with "mental disorder", or "psychiatric disorders" the term "Neuropsychiatric disorders, encompasses any anxiety disorder (for example Panic Attack, Agoraphobia, Panic Disorder Without Agoraphobia, Panic Disorder With Agaropholsia, Agoraphobia Without a History of Panic Disorder, Specific Phobia, Social Phobia, Obsssive-Compulsive Disorder, Postraumatic Stress Disorder, Acute Stress Disorder, Generalized Anxiety Disorder, Anxiety Disorder Due to a General Medical Condition, and Substance-Induced Anxiety Disorder and Anxiety Disorder Not Otherwise Specified), any psychotic disorder (for example Schizophrenia, Schizophreniform Disorder, Schizoaffective Disorder, Delusional Disorder, Brief Psychotic Disorder, Shared Psychotic Disorder, Psychotic Disorder Due to a General Medical Condition, and Substance-Induced Psychotic Disorder and Psychotic Disorder Not Otherwise Specified) and any mood disorder (Major Depressive Disorder, Dysthymic Disorder, Depressive Disorder Not Otherwise Specified, Bipolar I Disorder, Bipolar II Disorder, Cyclothymic Disorder, Mood Disorder Due to a General Medical Condition, Substance-Induced Mood Disorder and Mood Disorder Not Otherwise Specified) known in the art. "Neuropsychiatric Disorder" is used herein to refer to any neurological disease or mental disorder in which a major symptom is the occurrence of repetitive unwanted, intrusive or involuntary stereotyped thoughts, perceptions, or behaviors. Exemplary symptoms of these disorders specifically include obsessions, ruminations about fears of disease, posttraumatic "flashbacks", experiences of recurrent pain in the absence of somatic disease, compulsions, and tics. Particularly preferred mental disorders with such symptoms as characteristic features include Obsessive-Compulsive Disorder (OCD), Posttraumatic Stress Disorder (PTSD), Hypochondriasis, Pain Disorder, and Somatization Disorder. Other preferred mental disorders that may have such symptoms include, but are not limited to Schizophrenia, Major Depression, and Bipolar Disorder. Neurological Disorders characterized by such symptoms include tics, Gilles de la Tourette Syndrome (TS), and focal dystonia; other neurological disorders that may have such symptoms include Huntington's disease.

"Posttraumatic stress disorder": The term "posttraumatic stress disorder" or "PTSD" as used herein to describe an anxiety disorder characterized by an immediate or delayed response to a catastrophic event, characterized by re-experiencing the trauma, psychic numbing or avoidance of stimuli associated with the trauma, and increased arousal. Re-experiencing phenomena include intrusive memories, flashbacks, nightmares, and psychological or physiological distress in response to trauma reminders. Such responses are anxiety producing and can have significant impact, both chronic and acute, on a patient's quality of life and physical and emotional health.

"Obsessive-compulsive disorder": "Obsessive-compulsive disorder" or "OCD" is an anxiety disorder characterized by recurrent obsessions or compulsions sufficient to cause marked distress in the individual. They are time-consuming, or they significantly interfere with the person's normal functioning, social activities, or relationships. Obsessions are recurrent ideas, thoughts, images, or impulses that enter the mind and are persistent, intrusive, and unwelcome. Attempts are made to ignore or suppress the thoughts, or to neutralize them with some other thought or action. The individual recognizes them as a product of his or her own mind. Compulsions are repetitive, purposeful behaviors performed in response to an obsession, and are designed to neutralize or prevent discomfort or some dreaded event or situation. A common obsession concerns thoughts of contamination; excessive handwashing is a common compulsion.

"Tardive dyskinesia": As used herein "tardive dyskinesia" is meant to include tardive dystonia and other movement disorders related to long-term neuroleptic use. The abbreviation TD may be used in place of the term "tardive dyskinesia".

"Tourette's syndrome": "Tourette's syndrome" as used herein is synonymous with "Gilles de la Tourette syndromes", "Tourette syndrome", "Tourette disorder", and similar expressions. The abbreviation TS may be used in place of any of these terms.

"Blepharospasm": As used herein, "blepharospasm" includes Meige syndrome, which is a combination of blepharospasm and dystonia of the face and/or neck.

"Tic disorder": "Tic disorder" as used herein, refers to an abrupt repetitive movement, gesture, or utterance that often mimics a fragment of purposeful behavior. Tics are characterized by stereotyped, repetitive, but irregularly rhythmic involuntary movements. They include both motor tics and vocal (phonic) tics. Tic disorders include, for example, simple tics, multiple tics and Gilles de la Tourette syndrome, defined as multiple tics with vocalizations.

"Movement disorder": "Movement disorder", as used herein, is used to refer to all forms of abnormal and involuntary movements, including vocalizations. Movement disorders include, for example, tardive dyskinesia (TD), tics, Gilles de la Tourette syndrome (TS), Parkinson's disease, Huntington's disease, and focal dystonias such as blepharospasm.

DETAILED DESCRIPTION OF THE INVENTION

The present invention relates to treatment of any neuropsychiatric disorder (e.g. any anxiety disorder, any psychotic disorder, any mood disorder or any somatoform disorder) in which a major symptom is the occurrence of repetitive unwanted, intrusive or involuntary stereotyped thoughts, perceptions or behaviors. In particular, the present invention provides treatments for neuropsychiatric disorders including PTSD, OCD, and somatoform disorders, and treatment for such repetitive thoughts, perceptions, and behaviors when they occur as symptoms of other disorders including for example Schizophrenia, Major Depression, and Bipolar Disorder. In one aspect of the present invention, I have discovered that an agent used for the treatment of abstinent alcoholics, and more recently for the treatment of movement disorders, (see pending U.S. patent application, Ser. No. 09/006,641), and not contemplated for use in treatment of neuropsychiatric disorders is effective in reducing symptoms associated with neuropsychiatric disorders.

Several years ago, I hypothesized that tardive dyskinesia, other neuroleptic-induced movement disorders, and spontaneous movement disorders that resemble them, represent a form of non-linear oscillation in neural circuits involving the basal ganglia, and that oscillation might be reduced by agents that block excitatory neurotransmission. PET scan studies have demonstrated increased metabolism in the globus pallidus and primary motor cortex in schizophrenic patients with TD, but not in those without TD (Pahl et al., *J Neuropsych Clin Neurosci* 7:457, 1995). This suggests that TD is associated with hyperactivity in a motor control circuit, which functions as a nonlinear oscillator.

As noted above, I advanced the hypothesis that agents that act to reduce the gain in a motor control circuit through the striatum, can have a beneficial action on TD and related movement disorders (e.g., Tourette's syndrome and tics). GABA is an inhibitory neurotransmitter in the striatum. Support for my hypothesis comes from animal evidence indicating that agents that directly or indirectly stimulate GABA receptors can decrease neuroleptic-induced dyskinesias (Gao et al. *J Neural Transmission* 95:63, 1993; Stoessl, *Pharmacol. Biochem. Behav.*, 54:541, 1996). Rats with neuroleptic-induced dyskinesia demonstrate decreased striatal levels of glutamic acid decarboxylase, the rate-limiting enzyme in the production of GABA (Delfs et al., *Exp. Neurol.*, 133:175, 1995).

I proposed, without limiting the biochemical mechanism of the invention, that drugs acting to reduce the gain in the hypothesized oscillator circuit would reduce the involuntary movements of tardive dyskinesia. GABA, glutamate, and dopamine are the principal neurotransmitters in the circuit. Other neurotransmitters, including norepinephrine, serotonin, acetylcholine and endogenous opiates are hypothesized to have indirect actions on the oscillator circuit. In my co-pending patent applications, Ser. Nos. 08/861,801 and 09/193,892, the teachings of which are incorporated herein by reference, I disclosed that certain antagonists of excitatory neurotransmitters are effective in treating both the movement and cognitive disorders associated with TD, tardive dystonia, and related movement disorders. In the present application, I propose in a non-limiting fashion that antagonist-type drugs that act to reduce the gain in the oscillator circuit can be used to treat a wide variety of neuropsychiatric disorders that fall under a broad range of classifications. Support for this hypothesis is set forth below.

Relating Neuropsychiatric Disorders to Movement Disorders

There are noteworthy similarities between PTSD and tics. Like PTSD, tics involves the repetitive involuntary, stereotyped phenomena—thoughts and images in the case of PTSD and simple non-purposeful movements in the case of tics. In both cases, neocortical representations are activated by striatal or limbic input. Tics can be temporarily suppressed with conscious effort. However, when the effort stops or when tics break through despite an effort at suppression, there often is a rebound in frequency or intensity. A similar phenomenon has been demonstrated with intrusive imagery in an experimental model of PTSD phenomena—recall by subjects of images from a distressing film (Davies M I; Clark D M: Thought suppression produces a rebound effect with analogue post-traumatic intrusions. Behav Res Ther, 36:571–82, June 1998).

There is also a strong association of OCD with movement disorders. OCD is associated with Gilles de la Tourette syndrome (Tourette syndrome, TS), as well as with several other basal ganglia diseases including Sydenham's chorea and Huntington's disease. There is strong evidence of a link between OCD and motor tics. While estimates of the occurrence of OCD in patients with TS vary from 5% to over 50%, all estimates are significantly higher than the prevalence of OCD in the general population. Shared clinical features between OCD and TS include "waxing and waning of symptoms, early age at onset, ego-dystonic behavior (i.e., behavior contrary to an individuals conscious preferences), worsening with depression and anxiety, and their occurrence in the same families" (Robertson and Yakely, supra). Genetic studies suggest that in some families, there is a single autosomal dominant gene that can be expressed phenotypically as TS, OCD, or both. TS is most often treated with dopamine antagonists and OCD with serotonin reuptake inhibitors (SRIs). However, the addition of dopamine antagonists can augment the therapeutic efficacy of SRIs in OCD, and the addition of SSRIs can augment the efficacy of dopamine antagonists in TS. All of these considerations support the idea that there are overlapping physiologic mechanisms for OCD and TS.

Both tics and OCD can be produced by the CNS effects of an autoimmune reaction to infection with Group A beta-hemolytic streptococcus—the PANDAS syndrome—Pediatric AutoImmune Disorders Associated with Streptococcus. (Swedo S E, et al: Pediatric autoimmune neuropsychiatric disorders associated with streptococcal infections: clinical description of the first 50 cases. Am J Psychiatry, 155:264–71, February 1998). Similarly, traumatic brain injury can lead to the simultaneous new onset of tics and OCD symptoms (Krauss J K; Jankovic J: Tics secondary to craniocerebral trauma. Mov Disord, 12:776–82, September 1997).

OCD symptoms were compared between patients with blepharospasm, a focal dystonia caused by basal ganglia dysfunction, and hemifacial spasm, a syndrome with superficially similar symptoms but due to peripheral nerve dysfunction. The blepharospasm patients had significantly more OCD symptoms on a symptom check list (Broocks, et al.: Higher prevalence of obsessive-compulsive symptoms in patients with blepharospasm than in patients with hemifacial spasm. Am J Psychiatry, 155:555–7, April 1998).

OCD is not only associated with TS, but obsessive-compulsive phenomena share common clinical features with tics. Both involve repetitive, stereotyped, involuntary phenomena. In the case of OCD, these are thoughts or purposeful motor sequences (compulsive rituals); in the case of tics they are simpler, non-purposeful movements. Both involve activation of neocortical representations by limbic or striatal inputs.

As noted above, there are clinical and physiological similarities between tics, the obsessions and rituals of OCD, and the intrusive thoughts and images of PTSD. Although, the pathophysiologic, epidemiological and clinical association of tics and OCD is somewhat stronger than that of PTSD with tics, both PTSD and OCD can be correlated with tics. Therefore, I reasoned that treatments helpful for tics would be helpful for intrusive phenomena in PTSD, and that if they were helpful in PTSD, they would also be helpful for the obsessions and compulsions of OCD.

A link between movement disorders and somatoform disorders can be made through the correlation between somatoform disorders, PTSD and OCD. A few relevant studies are as follows:

1) Rogers et al. studied the prevalence of somatoform disorders in a sample of 654 patients with anxiety disorders. Thirty-six (5.5%) of the subjects had past or current somatoform disorders. The subjects with somatoform disorders were significantly more likely to have histories of posttraumatic stress disorder (22% vs. 8%) (Rogers M R, et al.: Prevalence of somatoform disorders in a large sample of patients with anxiety disorders. Psychosomatics, 37(1):17–22 January–February 1996).

2) Women with chronic pelvic pain not explained by a thorough gynecological evaluation were compared with controls who were either pain-free, or had pain in some other area of the body. The women with chronic pelvic pain had a much higher rate of past sexual abuse than those in either of the other two groups (Collett B J, et al.: A comparative study of women with chronic pelvic pain, chronic nonpelvic pain and those with no history of pain attending general practitioners. Br J Obstet Gynaecol, 105(1):87–92 January 1998).

3) A study of 45 patients with pseudoseizures (non-epileptic seizures), with the pseudoseizure diagnosis confirmed by simultaneous video and EEG recording, revealed a 49% prevalence of posttraumatic stress disorder (Bowman E S; Markand O N: Psychodynamics and psychiatric diagnoses of pseudoseizure subjects. Am J Psychiatry, 153(1):57–63 January 1996).

4) A study of 442 patients with OCD revealed that 12% had a concurrent diagnosis of body dysmorphic disorder. The authors concluded that the two disorders are "strongly related" (Simeon D, et al.: Body dysmorphic disorder in the DSM-IV field trial for obsessive-compulsive disorder. Am J Psychiatry, 152(8):1207–9 August 1995). As noted above, subsequent studies have shown that SRIs, the mainstay of treatment for OCD, are efficacious in the treatment of body dysmorphic disorder.

5) Women with chronic pelvic pain unexplained by a gynecologic evaluation show the same abnormality of hypothalamic-pituitary-adrenal regulation as seen in women with PTSD. Compared with normal controls, in both cases the adrenal produces less cortisol in response to ACTH, and cortisol suppresses more with a low dose of dexamethasone (Heim C et al.: Abuse-related posttraumatic stress disorder and alternations of the hypothalamic-pituitary-adrenal axis in women with chronic pelvic pain, psychosom Med. 60(3):309–318 May–June 1998).

6) A study of 256 college students demonstrated a positive correlation between self-reported nervous habits and tics, their awareness of bodily sensations, and their level of anxiety. (Woods D W, et al.: Habits, tics, and stuttering. Prevalence and relation to anxiety and somatic awareness. Behav Modif, 20(2):216–25 April 1996) While the direction of causality is not clear, the association is compatible with the idea that a common underlying physiological disturbance may predispose individuals to both tics and amplification of somatic symptoms.

Taken together, studies like these suggest that trauma can lead both to PTSD and to various somatoform disorders, and often to a combination of the two. There is an overlap in symptoms between hypochrondriasis, body dysmorphic disorder, and OCD (specifically with obsessions). Similarly, there is an overlap in symptoms between tics and OCD (specifically with compulsions). Individuals with hypochrondriasis or body dysmorphic disorder have obsessional thoughts about illness: or about their appearance. The symptoms of tics resemble simple compulsions. In all of these conditions there are recurrent, stereotyped, unwanted, intrusive or involuntary thoughts, perceptions, or behaviors. Moreover, all are associated with increased anxiety. These features suggest overlapping pathophysiology of the several conditions. The overlap in symptoms and mechanisms among the different disorders suggests that a treatment effective for PTSD, tics, and OCD would also be beneficial for somatoform disorders.

The Non-Obvious Leap—from Somatic Pain to Somatization.

Based on the physiology of pain transmission and modulation one would expect somatic pain to respond to a drug with combined GABA-A agonist and NMDA-glutamate antagonist properties, if the dosage of the drug were sufficient (Canavero S; Bonicalzi V: supra). However, somatization phenomena, with their similarities to PTSD, OCD, and tics, and with their putative generation by reverberating neural loops, might respond to dosages of such a drug that would not be enough to significantly affect somatic pain transmission. In fact, the 5 patients I personally treat with acamprosate for movement disorders all have had intercurrent illnesses with pain as a symptom. None have reported analgesic effects from the dosage of acamprosate (333 to 666 mg) that they take several times a day for their movement disorder.

Based on the considerations above, I submit that drugs with combined GABA-A agonist and NMDA-glutamate antagonist effects in appropriate proportion, will relieve symptoms of somatoform disorders at non-toxic dosages, and at dosages not necessarily associated with general analgesia. Of course, the effect of these drugs on symptoms other than pain is not implied at all by the animal experiments on GABA, glutamate, and spinal pain transmission.

Treatment of Neuropsychiatric Disorders

Based on this experience and the above reasoning, I administered acamprosate to a patient with PTSD (see Case Report 1). The patient enjoyed significant relief of PTSD symptoms, in a dose-related manner, without side effects. The response of PTSD symptoms was not due to a non-specific alteration of mood or anxiety level. In fact, the patient experienced relief of flashbacks, traumatic memories and emotional numbing on days when she felt depressed or anxious. Improvements were experienced in the areas of the frequency of flashbacks, intrusive thoughts about traumatic events, and psychic numbing. Moreover, the patient was capable of talking more freely about traumatic events and showed a reduction in self-injurious behavior and the severity of her startle response.

In a previous and co-pending Continuation-in part patent application, Ser. No. 09/193,892, I demonstrated that acamprosate, a combined GABA-A agonist/NMDA-glutamate antagonist had marked benefit in the treatment of tics. That benefit was enhanced by the addition of magnesium. The benefit of treatment with acamprosate was also improved by addition of an NMDA-glutamate antagonist (for example memantine). In another aspect, benefit of treatment with acamprosate could be improved by co-administration of another GABA-A agonist. One of ordinary skill in the art will recognize that magnesium, an NMDA antagonist or a GABA-A agonist can be combined not only with acamprosate, but with any agent (or combination of agents) that has both NMDA antagonist activity or GABA agonist activity. When treating movement disorders, I also observed that the synergy of GABA-A actions and NMDA actions enabled the acamprosate, with or without magnesium, to provide significant therapeutic actions at non-toxic dosages. Moreover, this synergy of effect was observed in the absence of a corresponding synergy of toxicity. I propose, by extension, that this synergy of beneficial effects without synergy of toxicity should occur with the combined use of GABA-A agonists and NMDA-glutamate antagonists to treat neuropsychiatric disorders.

In the current invention, I disclose that acamprosate, a GABA-receptor agonist that also diminishes the postsynaptic response of NMDA-type receptors to glutamate can reduce or ameliorate symptoms associated with PTSD, OCD, somatoform disorders (somatization disorder, conversion disorder, hypochondriasis, and body dysmorphic disorder), and other neuropsychiatric disorders including depression, mania, and schizophrenia, when these disorders have symptoms involving repetitive stereotyped thoughts, perceptions, and behaviors. An important example is major depression, which frequently is associated with repetitive rumination on guilty or pessimistic themes.

Alternatively, acamprosate and related compounds can be used to treat symptoms, for example repetitive, unwanted involuntary or intrusive, stereotyped thoughts, perceptions or behaviors that are associated with a movement disorder. Some examples of movement disorders that might display such symptoms include Tourette's syndrome, focal dystonia, Huntington's disease, Parkinson's disease, Sydenham's chorea, systemic lupus erythematosus, and drug-induced movement disorders.

According to the theory of the present invention, a GABA-A agonist with concurrent antagonist effects on NMDA-type glutamate transmission reduces the severity of symptoms associated with neuropsychiatric disorders, including PTSD and by extension OCD and somatoform disorders. In addition, I propose that acamprosate and other agents that both (i) decrease NMDA-type glutamate neurotransmission, and (ii) increase GABA-A receptor neurotransmission are useful in the treatment of PTSD, OCD, somatoform disorder and other neuropsychiatric disorders.

The class of drugs that have simultaneous, synergistic GABA-A agonism and NMDA antagonism at non-toxic dosages represent a major new class of therapeutic agents for neuropsychiatric disorders. I assert the novelty of the conception of these drugs as a 'breakthrough' in psychopharmacology. The principle advanced is that many important neuropsychiatric disorders involve the abnormal activity of polysynaptic neural loops through the cortex, striatum, and thalamus. Abnormal activity of these loops produce recurrent, stereotyped, and unwanted, intrusive, or involuntary thoughts, perceptions, and behaviors. Limbic structures such as the amygdala and anterior cingulate region are part of these circuits, or influence them. Synapses with GABA or glutamate as their principal transmitters, are part of these circuits. Or, GABA and glutamate modulate traffic at two or more synapses in these circuits. An excess or deficiency in GABA in the limbic system or basal ganglia, can contribute to a neuropsychiatric disorder. Because GABA-A agonism—increasing an inhibitory influence—is combined with NMDA antagonism—decreasing an excitatory influence—the gain in the circuit is diminished at two or more synapses, leading to a substantial decrease in activity in the circuit as a whole. Normal neural traffic not involving recurrent activity in these cortical-striatal-thalamic circuits is affected to a lesser degree than is the activity responsible for symptom production. This is true because normal traffic is not influenced at as many synapses. In addition, some of the drugs encompassed by this application may not reduce normal activity at individual synapses as much as they reduce excessive activity.

The invention disclosed here has a broad scope, comprising the use of drugs with a particular combination of actions for a specific therapeutic purpose. It is obvious to one skilled in the art that a variety of different compounds and delivery systems can be employed to embody the invention. Agents can be synthesized with two active moieties, one an NMDA antagonist and the other a GABA-A agonist. Or, agents with the desired combination of pharmacodynamic properties can be modified to improve their absorption, pharmacokinetics, or ability to cross the blood-brain barrier. Agents can be delivered by a variety of delivery systems, to improve reliability of absorption or convenience of administration.

Acamprosate (calcium N-acetylhomotaurinate) is the calcium salt of N-acetylhomotaurine, a derivative of the amino acid taurine. (Taurine is aminoethanesulfonic acid. Homotaurine is aminopropanesulfonic acid. Acetylhomotaurine is N-acetylaminopropanesulfonic acid.) It is used clinically in the treatment of abstinent alcoholics to reduce or inhibit their craving for alcohol. Acamprosate, which is chemically similar to the inhibitory neurotransmitter GABA, is a GABA agonist, particularly at GABA-A receptors. Moreover, it reduces the postsynaptic response of NMDA-type glutamate receptors and reduces calcium influxes through voltage-operated channels. (Wilde & Wagstaff, *Drugs,* 53:1039–53, 1997).

Acamprosate, because of its low toxicity, is a particularly attractive drug for use in treating patients that experience intolerable side effects when treated with the medications presently available for neuropsychiatric disorders. In controlled trials for alcoholism treatment involving 3,338 patients, acamprosate had no severe medical or neurological side effects. Indeed, the rate of subject dropout was identical in the group receiving acamprosate treatment and in the group receiving a placebo (Wilde and Wagstaff, *Drugs,* June, 53(6):1038–53, 1996). Many patients experience intolerable side effects from the SRIs, which currently are the standard treatment for Acamprosate can be used either as a substitute for SRIs, or to augment the efficacy of SRIs and permit the use of lower, better-tolerated dosages.

The above hypothesis regarding a motor control circuit involving GABA (via GABA-A receptors) and glutamate (via NMDA receptors) implies that any drug that is a GABA-A agonist and an NMDA-type glutamate antagonist can ameliorate neuropsychiatric disorders. Acamprosate (calcium N-acetylhomotaurinate) is a specific example of such a drug for which I offer direct evidence in humans of efficacy in the treatment of PTSD. Other examples of such drugs include other salts of N-acetylhomotaurine, and those derivatives of homotaurine and acetylhomotaurine that have similar effects on GABA-A and NMDA-type glutamate transmission, and pro-drugs that are metabolized in the liver, blood, or brain to yield N-acetylhomotaurinate or related compounds with similar pharmacodynamic properties.

Accordingly, a preferred embodiment of the present invention provides derivatives of homotaurine and N-acetylhomotaurine at effective and non-toxic doses to a patient for treatment of neuropsychiatric disorders. Particularly preferred are derivatives of acamprosate that are readily absorbed from the gastrointestinal tract. Acamprosate is irregularly absorbed from the GI tract, in part due to the polar, hydrophilic character of the acetylhomotaurinate ion. It is well known in the art that certain derivatives of drugs may be absorbed better and more reliably because they are more lipophilic. For example, esters prepared from the acetylhomotaurinate ion would be more lipophilic, and therefore would have greater and more predictable absorption through the membranes of the intestinal mucosa. If such an ester were nontoxic and naturally metabolized in the body, for example, cleaved by enzymes in the blood, liver or the brain, it would be particularly preferred as a vehicle for reliably delivering the acetylhomotaurinate ion to the brain. Furthermore, such derivatives as described above would have, in appropriate dosages, equal or greater efficacy in treating any neuropsychiatric disorder responsive to acamprosate. Alternatively, the drug may be covalently attached to a lipophilic molecule for better absorption.

Generally, any pro-drug with improved delivery of acamprosate would also be a preferred means of delivery according to the present invention. A particularly preferred form of acamprosate would be a derivative of acamprosate with a long half-life. Such a derivative of acamprosate would be clinically superior to acamprosate, because it could be taken once daily, rather than three or four times per day, as is necessary when acamprosate is used. An additional approach to lengthening the half-life of acamprosate or a related medication is to deliver it in a time-release capsule.

In another preferred embodiment, a pharmaceutical agent is selected from the group of agents that act as GABA-receptor agonists and also act to decrease NMDA receptor function by an indirect or modulatory mechanism such as, in a non-limiting fashion, acamprosate calcium (calcium N-acetylhomotaurinate), other salts of N-acetylhomotaurinate (e.g., magnesium N-acetylhomotaurinate or lithium N-acetylhomotaurinate), acetylhomotaurine base, other homotaurine derivatives that have similar pharmacodynamic actions on GABA and glutamate transmission, and pro-drugs that are metabolized in the liver, blood, or brain to yield N-acetylhomotaurinate or related compounds with similar pharmacodynamic actions on GABA and glutamate transmission. In another preferred embodiment, a pharmaceutical agent is selected from the group of agents that have the ability to reduce glutamate-produced excitatory post-synaptic potentials in striatal cells, including acamprosate and the range of similar compounds and pro-drugs described previously. In other preferred embodiments, a combination of two or more pharmaceutical agents is selected such that the combination acts concurrently to augment GABA transmission (particularly via GABA-A receptors) and to attenuate NMDA-type glutamate transmission (e.g., by non-competitive inhibition, or by indirect or modulatory effects on NMDA receptors). A fourth embodiment is to combine such a compound or mixture of compounds with memantine or a similar non-competitive NMDA-receptor blocking agent described in detail below. The combinations may be either mixtures, covalently-bound moieties with combined action, or pro-drugs metabolized in the blood, liver, or brain to release each member of the combination.

Magnesium ion, which blocks calcium channels, is known to be an NMDA-glutamate receptor antagonist. If a magnesium salt or chelate is given together with another NMDA antagonist, the action of the latter is enhanced. In particular, the present invention sets forth that supplementation with magnesium can augment the action of acamprosate in treatment of a neuropsychiatric disorder.

An efficacious drug treatment might not only treat PTSD, but might prevent it if given soon after stress. Trauma victims may be identified prospectively who are at particularly high risk for developing PTSD. These include those with a history of prior trauma in childhood, as well as those with acute stress reactions. For example, a rape victim might be at risk for developing PTSD and could be administered an effective dose of acamprosate in order to prevent the development of PTSD. In another embodiment, magnesium supplementation is used in conjunction with a GABA-A agonist to may delay the onset of PTSD in a person at risk, or the onset of another neuropsychiatric disorder in a person identified as being at risk for it. In yet another embodiment, supplementation with magnesium will reduce the symptoms associated with various neuropsychiatric disorders. The present invention teaches the use of a combined NMDA antagonist-GABA agonist strategy with or without magnesium administration for treating and preventing neuropsychiatric disorders.

According to the present invention magnesium supplementation will augment the therapeutic effects of other NMDA-type receptor antagonists and down-regulators (see Case Report 5). In one preferred embodiment, magnesium is administered with acamprosate (calcium N-acetylhomotaurine) to treat neuropsychiatric disorders. In a particularly preferred embodiment, the magnesium salt of N-acetylhomotaurine and the magnesium salts of those derivatives of N-acetylhomotaurine that similarly enhance GABA transmission and diminish NMDA-glutamate neurotransmission, are effective treatments for neuropsychiatric disorders.

It will be recognized by those skilled in the art that for all conditions for which calcium N-acetylhomotaurinate is an effective treatment, magnesium N-acetylhomotaurinate, and the magnesium salts of those derivatives of N-acetylhomotaurine that have similar effects on GABA neurotransmission and NMDA-glutamate neurotransmission, will also be effective treatments. One specific instance of such a compound is one that has two active moieties, one that is a GABA-A agonist and another that is an NMDA antagonist. In the body, the compound may either remain intact, or may be metabolized into two compounds, one with GABA-A agonist activity and the other with NMDA antagonist activity. Alternatively, any magnesium salt or chelate may be administered with any salt of a derivative of homotaurine or N-acetylhomotaurine that has both NMDA antagonist and GABA-A agonist activity, to treat neuropsychiatric disorders. In one non-limiting example, a pill containing the appropriate dose of acamprosate together with the appropriate dose of magnesium may be formulated and administered to a patient with a neuropsychiatric disorder. In other preferred embodiments, an agent that has NMDA antagonist activity and GABA agonist activity is combined with the appropriate dose of magnesium in a pill. In yet another preferred embodiment, an NMDA antagonist is combined with a GABA agonist at an appropriate dose of magnesium in the form of a pill. One of ordinary skill in the art will recognize that the composition of administration is not limited to a pill, but can also be a syrup, an elixir, a liquid, a tablet, a time-release capsule, an aerosol or a transdermal patch.

The ratio of acamprosate to magnesium can be varied to optimize the therapeutic synergy of the two ingredients. I propose that the effective dose ranges will be similar for treatment of neuropsychiatric disorders as movement disorders, but some variation may exist and dose ranges may be determined experimentally by those having ordinary skill in the art. Magnesium N-aceytlhomotaurinate (Durlach, supra; 1980), with a magnesium:acetylhomotaurinate ratio of approximately 1:20 by weight, does not optimize the therapeutic effect of the two components for treatment of movement disorders (see U.S. patent applications Ser. Nos. 09/006,641 and 09/193,892 incorporated herein by reference). At typical therapeutic dosages of acetylhomotaurinate, the amount of magnesium is too low to have therapeutically-relevant effects on glutamate transmission. In my experience, I have had excellent therapeutic results from combining a 2 gram daily dosage of acamprosate with 1 gram of elemental magnesium, given as a salt or chelate (see U.S. patent application Ser. No. 09/193,892). This combination gives better relief of both TD and tics than 2 grams of acamprosate alone. I have also demonstrated that a single dose of 300 mg of magnesium will augment the therapeutic effect of a single 666 mg dose of acamprosate. One of ordinary skill in the art would expect the dose ranges determined to be effective for treating movement disorders to also be effective for treating other neuropsychiatric disorders, since the hypothesized mechanism of therapeutic action is the same.

Allowing for variations in individual response, and variations in the intestinal absorption of both acamprosate and magnesium, I assert that the optimal ratio of Mg:acetylhomotaurinate for an individual patient for treatment of neuropsychiatric disorders will be somewhere between 1:6 and 1:1. Lower ratios of magnesium to acamprosate are unlikely to boost the therapeutic effect of acamprosate significantly, and higher ratios than 1:1 are likely to produce magnesium toxicity (or at least GI intolerance) at a typical daily acamprosate dose of 2 grams. Although magnesium N-acetylhomotaurinate may be slightly more efficacious than calcium N-acetylhomotaurinate for treatment of neuropsychiatric disorders, in the present application we are effectively increasing the magnesium content of acamprosate and related compounds by administering magnesium ion (as a salt or chelate) in combination with a salt of N-acetylhomotaurinate, because there is a significant benefit to administering a higher ratio of magnesium to acamprosate than is present in the magnesium salt of acamprosate.

Another aspect of the present invention involves prevention of neuropsychiatric disorders, including anxiety disorders, psychotic disorders, mood disorders and somatoform disorders, with an agent or combination of agents that have simultaneous NMDA antagonist activity and GABA-A agonist activity without coadministration of magnesium. In one preferred embodiment of this aspect of the invention, such NMDA antagonist/GABA-A agonist combinations are used to prevent the development or aggravation of a neuropsychiatric disorder, for example in a patient showing preliminary symptoms of a neuropsychiatric disorder. In another preferred embodiment of this aspect of the invention, the NMDA antagonist/GABA-A agonist combined activities are used to prevent the development of a neuropsychiatric disorder, (e.g., PTSD) following stress. In a particularly preferred embodiment, agents or combinations of agents with NMDA antagonist/GABA-A agonist activity are administered to a patient at risk for developing a neuropsychiatric disorder, such as PTSD, to prevent the complications of substance abuse and somatization. Specifically, the prevention of alcoholism subsequent to extreme stress is particularly desirable. Alcoholism often develops as a complication of PTSD and/or following a traumatic event in a person's life. In order to prevent the development of substance abuse after trauma, the patient who experienced the traumatic event is treated with an agent with combined NMDA antagonist/GABA-A agonist activity shortly after the occurrence of the traumatic event. The value of acamprosate in treating abstinent alcoholics is well known. However, the use of acamprosate in preventing alcoholism in persons at risk has not been proposed hitherto.

One of ordinary skill in the art will recognize that the present invention is not limited to a method of treating PTSD, OCD and other neuropsychiatric disorders with any agent that reduces NMDA-type glutamate neurotransmission and increases GABA neurotransmission via direct effects on GABA and NMDA receptors. The invention also comprises the use of agents that modify NMDA-glutamate and GABA transmission in the same direction through indirect effects on receptors (i.e., via pre-synaptic effects on neurotransmitter release, allosteric modulation of the receptor site, or effects on the intracellular response to the binding of the transmitter to the receptor), presynaptic effects on transmitter release, inhibition of GABA re-uptake, etc. It will be obvious to one skilled in the art that a range of derivatives and pro-drugs all should be therapeutically effective, as long as they have a sufficient effect on GABA-A and NMDA-glutamate transmission at non-toxic dosages. Any compound or mixture that shares the effects on glutamate and GABA transmission hypothesized to underlie the therapeutic effects of acamprosate is within the scope of the presently claimed invention. It does not matter how a drug, pro-drug or mixture thereof decreases NMDA-glutamate neurotransmission and increases GABA neurotransmission, only that it improves symptoms associated with neuropsychiatric disorders at tolerably non-toxic (e.g., free from toxicity unacceptable side effects) doses.

As discussed previously, the inventive treatment can be used to treat any neuropsychiatric disorder that involves as symptoms unwanted, intrusive, or involuntary repetitive, stereotyped thoughts, perceptions, or behaviors. Furthermore, the inventive treatment may be used to improve or eliminate symptoms that are consequences of such neuropsychiatric disorders, for example, cognitive dysfunction or abnormalities of motivation, mood, or impulse control. The basal ganglia, including the striatum, are a point of intersection of motor, cognitive, and emotional circuits. Diseases of the basal ganglia frequently involve cognitive, emotional, behavioral, and motivational changes, as well as motor dysfunction. The limbic system, including the amygdala and anterior cingulate region can also influence this circuit. The treatments advanced in this invention are effective for the symptoms of several disorders involving dysfunction of the basal ganglia or the limbic system or circuits through them. It can be expected that these treatments will ameliorate some of the other symptoms that accompany basal ganglia and limbic system disorders.

The present invention will now be illustrated by the following non-limiting example:

Case Report

I administered acamprosate to a 33-year old woman with PTSD. This patient has PTSD on account of several incidents of sexual abuse in childhood and adolescence. Her symptoms included intrusive imagery of episodes of abuse (flashbacks), intrusive thoughts about episodes of abuse (traumatic memories), nightmares, increased startle response, anxiety, depression, avoidance of the company of men, emotional numbing, suicidal ideation, and self-injurious or risky behavior (e.g. cutting herself, reckless driving). The above symptoms were not relieved by any of large number of medications, including antipsychotic drugs (neuroleptics), antidepressants, benzodiazepines, and anti-epileptic drugs.

In March of 1998, the patient began acamprosate at a dosage of 333 mg three times a day. The dose was advanced gradually to 666 mg three times a day. On this dose, the patient had less anxiety, less suicidal ideation, fewer flashbacks of traumatic events, fewer intrusive thoughts of abuse, less psychic numbness, and greater ability to talk about the traumatic events that precipitated her PTSD. Additional doses of 666 mg of acamprosate, taken as needed, relieved psychic tension, hopelessness, suicidal ideation, and psychic numbing precipitated by reminders of her trauma.

The patient's PTSD symptoms continued to respond to treatment with acamprosate over a 1-year period from March, 1998 through March, 1999. Over this time, gradual dosage reductions were attempted to see whether the medication were still necessary, and if it were, to determine the minimum effective dose. Her symptoms responded in a dose-related manner that was replicated several times.

The response of specific PTSD symptoms to different dosages of acamprosate is now described. Symptom severity was rated semi-quantitatively, based on a consensus of physician and patient regarding the intensity of symptoms during the week preceding the date of rating. The scale of symptom severity ranges from 0 to ++++, with ++++ being the most severe.

| | 333 mg three times a day | 333 mg four times a day | 333 mg five times a day | 333 mg six times a day |
|---|---|---|---|---|
| Flashbacks | ++++ | +++ | ++ | + |
| Intrusive thoughts about traumatic events | +++ | ++ | + | + |
| Psychic numbing | +++ | ++ | + | + |
| Ability to talk freely about life events and personal issues | poor | fair | fair | good |
| Self-injurious and risky behavior | ++ | + | 0 | 0 |
| Startle Response | ++ | | + | + |

SUMMARY

The Case Report demonstrates that acamprosate is effective for treatment of PTSD at effective and non-toxic dosages. Administration of acamprosate to a patient with PTSD resulted in a striking response with respect to a several recurrent thoughts, perceptions, and behaviors characteristic of PTSD, and not responsive in her case to conventional psychiatric medications. The patient's response to acamprosate treatment, coupled a previously-reported case of the efficacy of acamprosate in a patient with a simple tic, provides evidence and suggestion that patients with other neuropsychiatric disorders, for example ocd and somatoform disorders, will receive similar benefit from acamprosate or similar agents or combination of agents with nmda antagonist activity and GABA-A agonist activity

I claim the following:

1. A method for treating symptoms of anxiety disorders comprising steps of: administering to a patient with an anxiety disorder an effective and non-toxic dose of an agent that increases GABA-A neurotransmission and decreases NMDA-glutamate neurotransmission, wherein the dose ranges from between approximately 1 gram per day to approximately 2.6 grams per day wherein the agent is selected from the group consisting of: calcium N-acetylhomotaurinate, magnesium N-acetylhomotaurinate, lithium N-acetyihomotaurinate, salts of N-acetylhomotaurine, and acetyihomotaurine base and derivatives of acetyihomotaurinate that enhance GABA-A transmission and reduce NMDA-type glutamate transmission.

2. A method for preventing symptoms of anxiety disorders in a patient in need thereof comprising steps of:

preventing symptoms of anxiety disorders by administering to the patient an effective and non-toxic dose of an agent that increases GABA-A neurotransmission and decreases NMDA-glutamate neurotransmission, wherein the agent is selected from the group consisting of: calcium N-acetylhomotaurinate, magnesium N-acetylhomotaurinate, lithium N-acetylhomotaurinate, salts of N-acetylhomotaurine, acetyihomotaurine base and derivatives of acetyihomotaurinate that enhance GABA-A transmission and reduce NMDA-type glutamate transmission.

3. The method of claim 1 or 2, wherein said symptoms are selected from the group consisting of repetitive and stereotyped unwanted thoughts; repetitive and stereotyped unwanted perceptions; repetitive and stereotyped intrusive thoughts; repetitive and stereotyped intrusive perceptions; repetitive and stereotyped involuntary movements; repetitive and stereotyped involuntary behaviors; repetitive and stereotyped compulsive movements; and repetitive and stereotyped compulsive behaviors.

4. The method of claim 1 or 2, wherein said anxiety disorder is selected from the group consisting of: post-traumatic stress disorder and obsessive-compulsive disorder.

5. The method of claim 1 or 2, wherein the agent increases GABA-A neurotransmission and decreases NMDA-glutamate neurotransmission with synergy of therapeutic efficacy and without synergy of toxicity.

6. The method of claim 1 or 2, wherein the agent is available in blood.

7. The method of claim 1 or 2, wherein the agent is available in the brain.

8. The method of claim 1 or 2, wherein the agent is a pro-drug metabolized in the body to release acetylhomotaurinate ion into the body.

* * * * *